United States Patent
Jung et al.

(10) Patent No.: US 8,663,736 B2
(45) Date of Patent: Mar. 4, 2014

(54) GERMANIUM COMPLEXES WITH AMIDINE DERIVATIVE LIGAND AND PROCESS FOR PREPARING THE SAME

(75) Inventors: Jae Sun Jung, Daejeon (KR); Su Hyong Yun, Chuncheonsi (KR); Minchan Kim, Daegu (KR); Sung Won Han, Seoul (KR); Yong Joo Park, Gongju-si (KR); Su Jung Shin, Incheon (KR); Ki Whan Sung, Jeonllabuk-do (KR); Sang Kyung Lee, Yongin-si (KR)

(73) Assignee: Soulbrain Sigma-Aldrich Ltd., Chungcheongnam-do (KR)

( * ) Notice: Subject to any disclaimer, the term of this patent is extended or adjusted under 35 U.S.C. 154(b) by 425 days.

(21) Appl. No.: 13/143,621

(22) PCT Filed: Jan. 7, 2010

(86) PCT No.: PCT/KR2010/000105
§ 371 (c)(1),
(2), (4) Date: Jul. 7, 2011

(87) PCT Pub. No.: WO2010/079979
PCT Pub. Date: Jul. 15, 2010

(65) Prior Publication Data
US 2011/0268881 A1 Nov. 3, 2011

(30) Foreign Application Priority Data
Jan. 8, 2009 (KR) .......................... 10-2009-0001645

(51) Int. Cl.
C23C 16/18 (2006.01)
C07F 7/30 (2006.01)

(52) U.S. Cl.
USPC ............... 427/255.35; 427/255.39; 556/36; 556/81

(58) Field of Classification Search
USPC ............... 427/255.35, 255.39; 556/36, 81
See application file for complete search history.

(56) References Cited

U.S. PATENT DOCUMENTS

| | | | |
|---|---|---|---|
| 7,727,884 B2 | 6/2010 | Bae et al. | |
| 2003/0075415 A1 | 4/2003 | Ito | |
| 2003/0111013 A1 | 6/2003 | Oosterlaken et al. | |
| 2008/0145978 A1* | 6/2008 | Laxman | 438/149 |
| 2009/0112009 A1* | 4/2009 | Chen et al. | 556/12 |
| 2009/0305458 A1* | 12/2009 | Hunks et al. | 438/102 |
| 2009/0324963 A1* | 12/2009 | Cordonier et al. | 428/426 |

FOREIGN PATENT DOCUMENTS

| | | |
|---|---|---|
| KR | 1020060074236 A | 3/2006 |
| KR | 100780865 B1 | 11/2007 |
| KR | 100860140 B1 | 9/2008 |
| WO | 2006012052 A2 | 2/2006 |
| WO | 2008057616 A2 | 5/2008 |
| WO | WO 2008/057616 * | 5/2008 |

OTHER PUBLICATIONS

Jones, Cameron, et al., "Synthesis, characterisation and reactivity of germanium(II) amidinate and guanidinate complexes". Dalton Transactions, 2008, 2871-2878.*
Shah, Alpa Y., et al., "Aerosol assisted chemical vapour deposition of germanium thin films using organogermanium carboxylates as precursors and formation of germania films". Bull. Mater. Sci., vol. 35, No. 3, Jun. 2012, pp. 365-368.*
Park, Ji-Soo, et al., "Growth of Ge thick layers on Si(001) substrates using reduced pressure chemical vapor deposition." Japanese Journal of Applied Physics, vol. 45, No. 11, 2006, pp. 8581-8585.*
Wu, Minxian, et al., "Electrodeposition of germanium from the ionic liquid 1-butyl-1-methylpyrrolidinium dicyanamide". Phys. Chem. Chem. Phys., 2013, 15, 4955-4964.*
Veprek et al., Challenges and Confusion in the Kinetics and Mechanism of Plasma Induced Deposition of a- and µc-Ge: H, Journal of Non-Crystalline Solids, 1991, pp. 779-782, vols. 137-138.
Suh et al., Synthesis of Tin Oxide Precursors and Related Germanium and Lead Compounds, Inorg. Chem., 1996, pp. 6164-6169, vol. 35.
Foley et al., Facile Formation of Rare Terminal Chalcogenido Germanium Complexes with Alkylamidinates as supporting Ligands, J. Am. Chem. Soc., 1997, pp. 10359-10363, vol. 119.
Foley et al., Synthesis and Structural Characterization of the First Trialkylguanidinate and Hexahydropyramidopyramidinate Complexes of Tin, Polyhedron, 2002, pp. 619-627, vol. 21.
Gerung et al., Anhydrous Solution synthesis of Germanium Nanocrystals from the Germanium(II) Precurser Ge[N(SiMe3)2]2, Chem. Commun., 2005, pp. 1914-1916.

* cited by examiner

Primary Examiner — Bret Chen
(74) Attorney, Agent, or Firm — The Webb Law Firm

(57) ABSTRACT

Provided is a germanium complex represented by Chemical Formula 1 wherein Y1 and Y2 are independently selected from R3, NR4R5 or OR6, and R1 through R6 independently represent (Ci-C7) alkyl. The provided germanium complex with an amidine derivative ligand is thermally stable, is highly volatile, and does not include halogen components. Therefore, it may be usefully used as a precursor to produce high-quality germanium thin film or germanium-containing compound thin film by metal organic chemical vapor deposition (MOCVD) or atomic layer deposition (ALD).

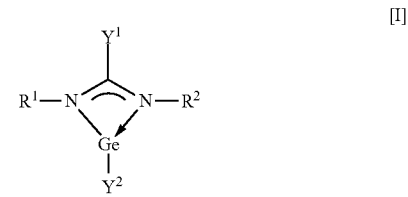

[I]

19 Claims, 8 Drawing Sheets

GERMANIUM COMPLEXES WITH AMIDINE DERIVATIVE LIGAND AND PROCESS FOR PREPARING THE SAME

TECHNICAL FIELD

The present invention relates to a novel germanium complex with an amidine derivative ligand and a method for preparing the same, more preferably to preparation of an asymmetric germanium complex useful as a precursor for preparing germanium thin film or germanium-containing compound thin film.

BACKGROUND ART

In preparation of thin film through thin film deposition, in particular in chemical vapor deposition and atomic layer deposition, highly pure precursors that can be easily deposited at low temperatures are required for ideal thin film deposition needed in semiconductor processes and various other fields. Especially, germanium precursors are used in silicon-germanium solar cells, optical coatings, or the like. Recently, they are used in various fields including the manufacture of GeSbTe (GST) thin film as next-generation semiconductor device.

In general, germane ($GeH_4$) is used as a germanium precursor in producing germanium thin film or germanium-containing compound thin film. Germane is toxic gas in standard condition and is difficult to handle. Therefore, it needs safety equipment for process application. In addition, it is restricted in use in semiconductor processes requiring low temperature, since a deposition temperature of about 500° C. or higher is necessary for chemical vapor deposition (CVD). For other organometallic germanium precursors, those with alkyl (R), alkoxy (OR) or cyclopentadiene (Cp) groups as ligand are reported. However, because large steric hindrance occurring due to the ligands, these precursors are solid at room temperature or tend to be associated with thin film contamination during deposition (Veprek, S., Glatz, F.; Knowitschny, R. *J. Non-Cryst. Solids* 1991, 137 and 138, 779; Seigi Suh and David M. Hoffman, *Inorg. Chem.* 1996, 35, 6164-6169; Henry Gerung, Scott D. Bunge, Timothy J. Boyle, C. Jeffrey Brinkerab and Sang M. Han, *Chem. Commun.*, 2005 1914-1916).

US Patent Application No. 2003/0111013 (Oosterlaken, et al.) discloses deposition methods of silicon germanium layer for thin film preparation using mono-, di-, tri- or tetrachlorogermane. However, these compounds are not appropriate for deposition of germanium because they are decomposed at low temperature.

Korean Patent Application No. 2007-0042805 (Changkyun Kim, et al.) discloses a method for preparing a germanium(II) complex with an aminoalkoxide ligand. This compound is a liquid material which is decomposed approximately at 236° C.

Recently, there have been patents and researches about the preparation of GST thin film and related precursor for the manufacture of phase-change random access memory (PRAM). PCT/US2007/063830 (Hunks, et al.) discloses deposition methods of GST thin film using a germanium precursor with an alkylamino ligand, and Korean Patent Application No. 2004/0112906 (Beom-seok Seo, at al.) discloses deposition methods of GST thin film using a germanium(IV) precursor with a silylamino ligand.

DISCLOSURE

Technical Problem

In order to solve the problems associated with the aforesaid germanium complexes, the inventors of the present invention have developed a new asymmetric germanium precursor with an amidine derivative ligand, having improved thermal stability and being capable of deposition at low temperature.

An object of the present invention is to provide a novel asymmetric germanium complex and a method for preparing the same. Another object of the present invention is to provide a method for preparing germanium thin film by using novel germanium complex capable of deposition at low temperature of below 300° C.

Technical Solution

The present invention relates to a germanium complex represented by Chemical Formula 1.

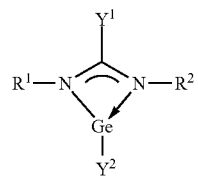

[Chemical Formula 1]

In Chemical Formula 1, $Y^1$ and $Y^2$ are independently selected from $R^3$, $NR^4R^5$ or $OR^6$, and $R^1$ through $R^6$ independently represent ($C_1$-$C_7$)alkyl.

The germanium complex according to the present invention is thermally stable, is highly volatile, and does not include halogen components. Therefore, it may be usefully used as a precursor to produce high-quality germanium thin film or germanium-containing compound thin film by metal organic chemical vapor deposition (MOCVD) or atomic layer deposition (ALD).

In the present invention, $Y^1$ and $Y^2$ may be independently selected from $-N(CH_3)_2$, $-N(CH_3)(CH_2CH_3)$, $-CH_3$, or $-C(CH_3)_3$, and $R^1$ through $R^2$ may independently represent methyl, ethyl, propyl or t-butyl. $Y^1$ and $Y^2$ may be the same ligand, but, more preferably, $Y^1$ and $Y^2$ may be different ligands.

More specifically, the germanium complex represented by Chemical Formula 1 may be selected from the following structures:

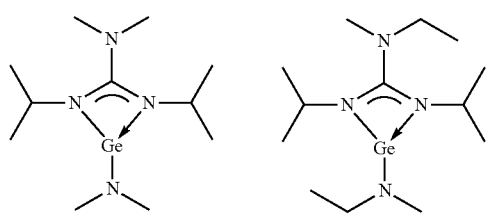

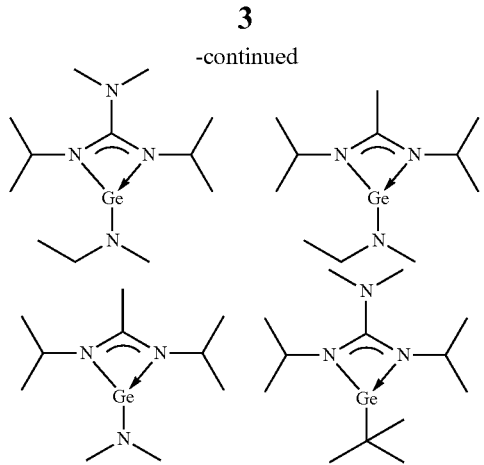

The germanium complex represented by Chemical Formula 1 according to the present invention may have various substituents introduced to the amidine ligand binding with the central metal germanium thus to control steric hindrance. As a result, intermolecular interaction may be reduced and the total molecular weight may be controlled thus to increase volatility. Such a structural characteristic provides the germanium complex according to the present invention with the following advantages. The germanium complex exists as liquid at room temperature, is highly soluble in organic solvents such as benzene, tetrahydrofuran, toluene, etc., and has good volatility. Accordingly, the germanium complex according to the present invention may be very useful as a precursor to produce germanium thin film or germanium-containing compound thin film.

Hereinafter, a method for preparing the germanium complex represented by Chemical Formula 1 according to the present invention will be described in detail. The germanium complex represented by Chemical Formula 1 according to the present invention may be prepared by a method commonly used in the related art. Although not particularly limited thereto, the present invention provides the following preparation method.

According to the present invention, a germanium complex may be prepared by a method comprising:

a) reacting an alkali metal salt represented by Chemical Formula 3 with an alkylcarbodiimide ($R^1NCNR^2$) compound represented by Chemical Formula 4 to prepare a complex represented by Chemical Formula 5; and b) adding to the complex represented by Chemical Formula 5 a germanium (II) halide and an alkali metal salt represented by Chemical Formula 6 to prepare a germanium complex represented by Chemical Formula 1:

$M^1Y^1$ [Chemical Formula 3]

$R^1NCNR^2$ [Chemical Formula 4]

[Chemical Formula 5]

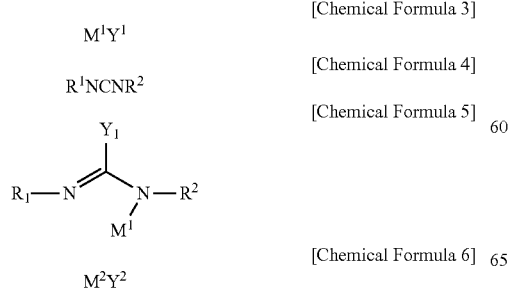

$M^2Y^2$ [Chemical Formula 6]

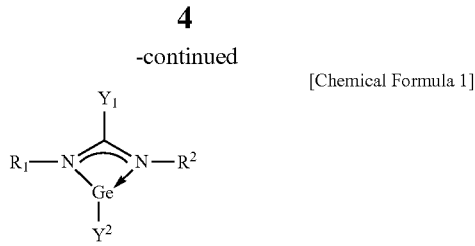

[Chemical Formula 1]

wherein $M^1$ and $M^2$ independently represent an alkali metal, $Y^1$ and $Y^2$ are independently selected from $R^3$, $NR^4R^5$ or $OR^6$, and $R^1$ through $R^6$ independently represent ($C_1$-$C_7$) alkyl.

In case $Y^1$ and $Y^2$ in Chemical Formula 1 are the same, Chemical Formula 1 may be rewritten as Chemical Formula 7.

More specifically, the germanium complex represented by Chemical Formula 7 may be selected from the following structures:

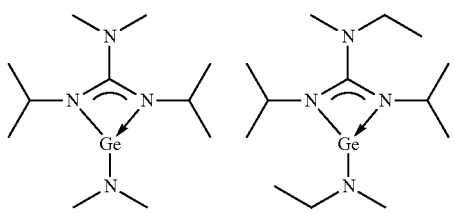

The germanium complex represented by Chemical Formula 7 may be prepared by the following preparation method.

The present invention provides a method for preparing a germanium complex, comprising:

reacting an alkali metal salt represented by Chemical Formula 3 with an alkylcarbodiimide ($R^1NCNR^2$) compound represented by Chemical Formula 4 to prepare a complex represented by Chemical Formula 5; and adding to the complex represented by Chemical Formula 5 a germanium(II) halide to prepare a germanium complex represented by Chemical Formula 7:

$M^1Y^1$ [Chemical Formula 3]

$R^1NCNR^2$ [Chemical Formula 4]

[Chemical Formula 5]

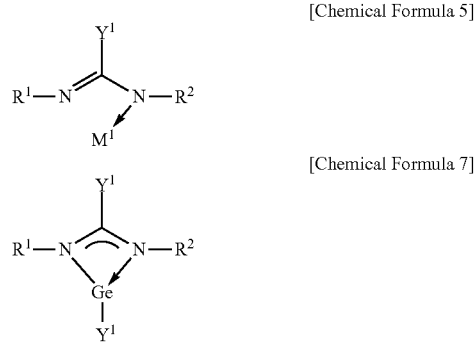

wherein $M^1$ represents an alkali metal, $Y^1$ is selected from $R^3$, $NR^4R^5$ or $OR^6$, and $R^1$ through $R^6$ independently represent ($C_1$-$C_7$)alkyl.

More specifically, the germanium(II) halide may be Ge(II)Br$_2$, Ge(II)Cl$_2$(dioxane) or Ge(II)I$_2$.

$M^1$ and $M^2$ may be independently lithium, sodium or potassium, more preferably lithium, and $Y^1$ and $Y^2$ may be independently —$N(CH_3)_2$, —$N(CH_3)(CH_2CH_3)$, —$CH_3$ or —$C(CH_3)_3$.

And, a specific example of the alkylcarbodiimide ($R^1NCNR^2$) represented by Chemical Formula 4 may be 1,3-diisopropylcarbodiimide.

In case $Y^1$ and $Y^2$ in Chemical Formula 1 are the same ligand, the germanium complex according to the present invention may be prepared by Scheme 1.

[Scheme 1]

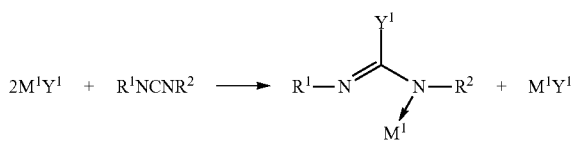

In Scheme 1, $M^1$ represents an alkali metal, $Y^1$ is selected from $R^3$, $NR^4R^5$ or $OR^6$, and $R^1$ through $R^6$ independently represent ($C_1$-$C_7$)alkyl.

According to Scheme 1, 2 molar equivalents of the alkali metal salt represented by Chemical Formula 3 is reacted with 1 molar equivalent of the alkylcarbodiimide represented by Chemical Formula 4 at low temperature, for example at −70° C., to obtain the complex represented by Chemical Formula 5. This reaction may be carried out by stirring for 3 to 12 hours.

In case $Y^1$ and $Y^2$ are the same ligand, the germanium complex according to the present invention may also be prepared by Scheme 2.

[Scheme 2]

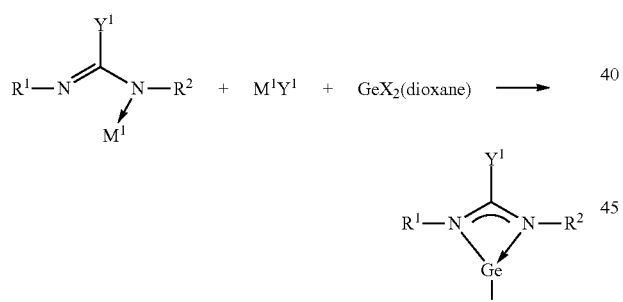

[Chemical Formula 7]

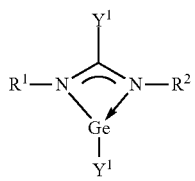

In case $Y^1$ and $Y^2$ are the same ligand, $Y^2$ may be represented by $Y^1$. As seen in Scheme 2, to an organic solvent including 1 molar equivalent of the alkali metal salt ($M^1Y^1$) represented by Chemical Formula 3, the complex represented by Chemical Formula 5 and a germanium(II) halide ($GeX_2$ (dioxane)) are added and reacted at low temperature, for example at −70° C., to obtain the germanium complex represented by Chemical Formula 7. This reaction may be carried out by stirring for 8 to 14 hours after adding the germanium (II) halide. The organic solvent that may be used in the present invention includes ether, hexane, toluene, etc. Prior to use, water and oxygen may be removed from these organic solvents according to the method known in the art. In Scheme 2, the germanium(II) halide $GeX_2$(dioxane) may be $Ge(II)Br_2$, $Ge(II)Cl_2$(dioxane) or $Ge(II)I_2$.

Hereinafter, a method for preparing the germanium complex according to the present invention in case $Y^1$ and $Y^2$ are different will be described in detail. In case $Y^1$ and $Y^2$ are different, the step a) of the preparation method of the present invention may be carried out according to Scheme 3.

[Scheme 3]

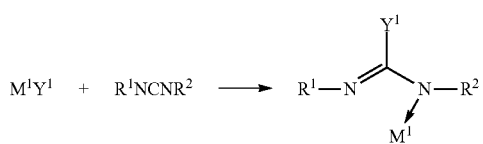

In Scheme 3, $M^1$, $Y^1$, $R^1$ and $R^2$ are the same as described above. Specifically, in Scheme 3, 1 molar equivalent of the alkali metal salt represented by Chemical Formula 3 is reacted with 1 molar equivalent of the alkylcarbodiimide represented by Chemical Formula 4 at low temperature, for example at −70° C., to obtain the complex represented by Chemical Formula 5. Subsequently, the step b) of the preparation method of the present invention may be carried out according to Scheme 4 and Scheme 5.

[Scheme 4]

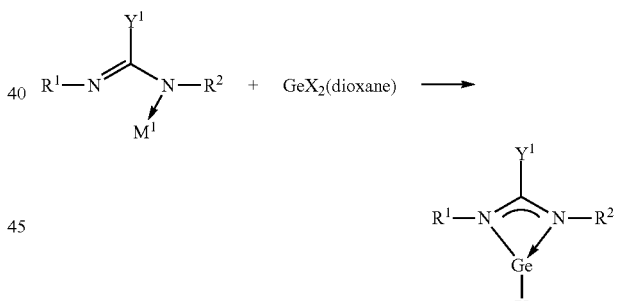

[Scheme 5]

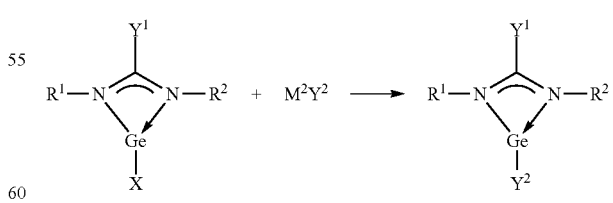

In Schemes 4 and 5, $M^1$ and $M^2$ independently represent an alkali metal, $Y^1$ and $Y^2$ are independently selected from $R^3$, $NR^4R^5$ or $OR^6$, and $R^1$ through $R^6$ independently represent ($C_1$-$C_7$)alkyl.

Thus prepared germanium complex according to the present invention may be liquid at room temperature, and $T_{1/2}$ (the temperature at which the weight of the sample reaches ½ of the original weight) in the thermogravimetric analysis (TGA) may be from 140 to 190° C. The structure of the germanium complex may be identified by nuclear magnetic resonance spectroscopy (NMR) or elemental analysis (EA).

The present invention further provides a method for preparing a germanium thin film, comprising: injecting the germanium complex represented by Chemical Formula 1 to a substrate provided in a reactor to prepare a germanium thin film by chemical vapor deposition (CVD) or ALD (atomic layer deposition). Here, the temperature of the substrate may range from 150 to 350° C. The substrate may be a silicon monocrystalline substrate or other semiconductor substrate. More specifically, a $TiN/SiO_2/Si$ substrate may be used.

The germanium thin film may be prepared using a reaction gas. However, thin film deposition is possible also without using a reaction gas. The reaction gas may be oxygen, hydrogen, ammonia gas, etc., but is not limited thereto. The inflow rate of the reaction gas may vary depending on the thin film to be deposited. The deposition pressure may range from 3 to 5 torr, but is not particularly limited thereto.

Advantageous Effects

The germanium complex with an amidine derivative according to the present invention has an asymmetric structure, exists as transparent liquid at room temperature, and may be easily obtained from a pure compound through vacuum distillation. In addition, the germanium complex with an amidine derivative according to the present invention is thermally stable, is highly volatile, and does not include halogen components. Therefore, it may be usefully used as a precursor to produce high-quality germanium thin film or germanium-containing compound thin film by metal organic chemical vapor deposition (MOCVD) or atomic layer deposition (ALD).

More specifically, the germanium complex according to the present invention may have various substituents introduced to the amidine ligand binding with the central metal germanium thus to control steric hindrance. As a result, intermolecular interaction may be reduced and the total molecular weight may be controlled thus to increase volatility.

In addition, since the germanium complex is pyrolyzable at low temperature in the absence of a reducing agent, it may be advantageously utilized as a precursor to produce high-quality germanium thin film or germanium-containing compound thin film.

DESCRIPTION OF DRAWINGS

The above and other objects, features and advantages of the present invention will become apparent from the following description of preferred embodiments given in conjunction with the accompanying drawings, in which.

MODE FOR INVENTION

Figure 1:
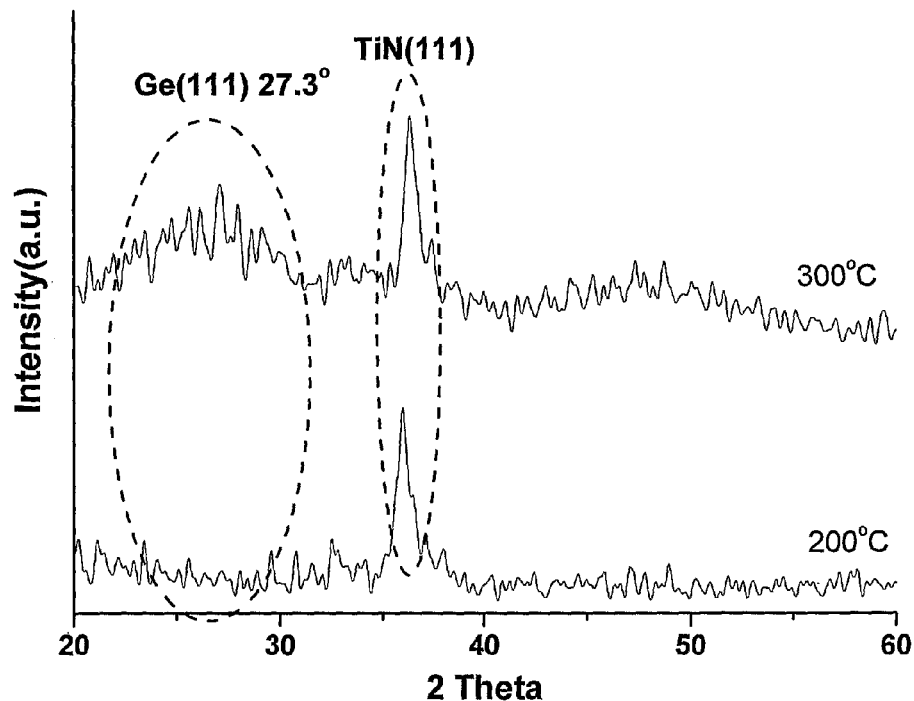
FIG. 1 shows X-ray diffraction (XRD) analysis result of the germanium thin films deposited in Example 7 and Example 9 according to the present invention.

The examples and experiments will now be described. The following examples and experiments are for illustrative purposes only and not intended to limit the scope of the present invention.

Example 1

Preparation of (N,N'-diisopropyl-dimethylguanidyl)(dimethylamino)germanium(II)

Anhydrous ether (60 mL) and lithium dimethylamide (3.40 g, 66.49 mmol) were added to a 250 mL Schlenk flask and cooled to −70° C. to prepare solution A. After slowly adding 1,3-diisopropylcarbodiimide (4.20 g, 33.24 mmol) dropwise to the solution A, the mixture was slowly warmed to room temperature and stirred for 4 hours to prepare solution B.

In another 250 mL Schlenk flask, anhydrous ether (100 mL) was added to dichlorogermanium-dioxane ($GeCl_2$(dioxane), 7.00 g, 30.22 mmol) and cooled to −70° C. to prepare solution C. After slowly adding dropwise the reaction solution (solution B) of lithium dimethylamide and 1,3-diisopropylcarbodiimide to the dichlorogermanium-dioxane solution (solution C), the mixture was slowly warmed to room temperature and stirred for 12 hours. After filtration, solvent was removed from the resulting filtrate at room temperature in vacuum. Thus obtained yellow liquid was distilled in vacuum (89° C./0.1 torr). (N,N'-diisopropyl-dimethylguanidyl)(dimethylamino)germanium(II) was obtained as colorless liquid.

Thus prepared (N,N'-diisopropyl-dimethylguanidyl)(dimethylamino)germanium(II) was subjected to thermogravimetric analysis (TGA). $T_{1/2}$ (the temperature at which the weight of the sample reaches ½ of the original weight) was 162° C.

Figure 4:
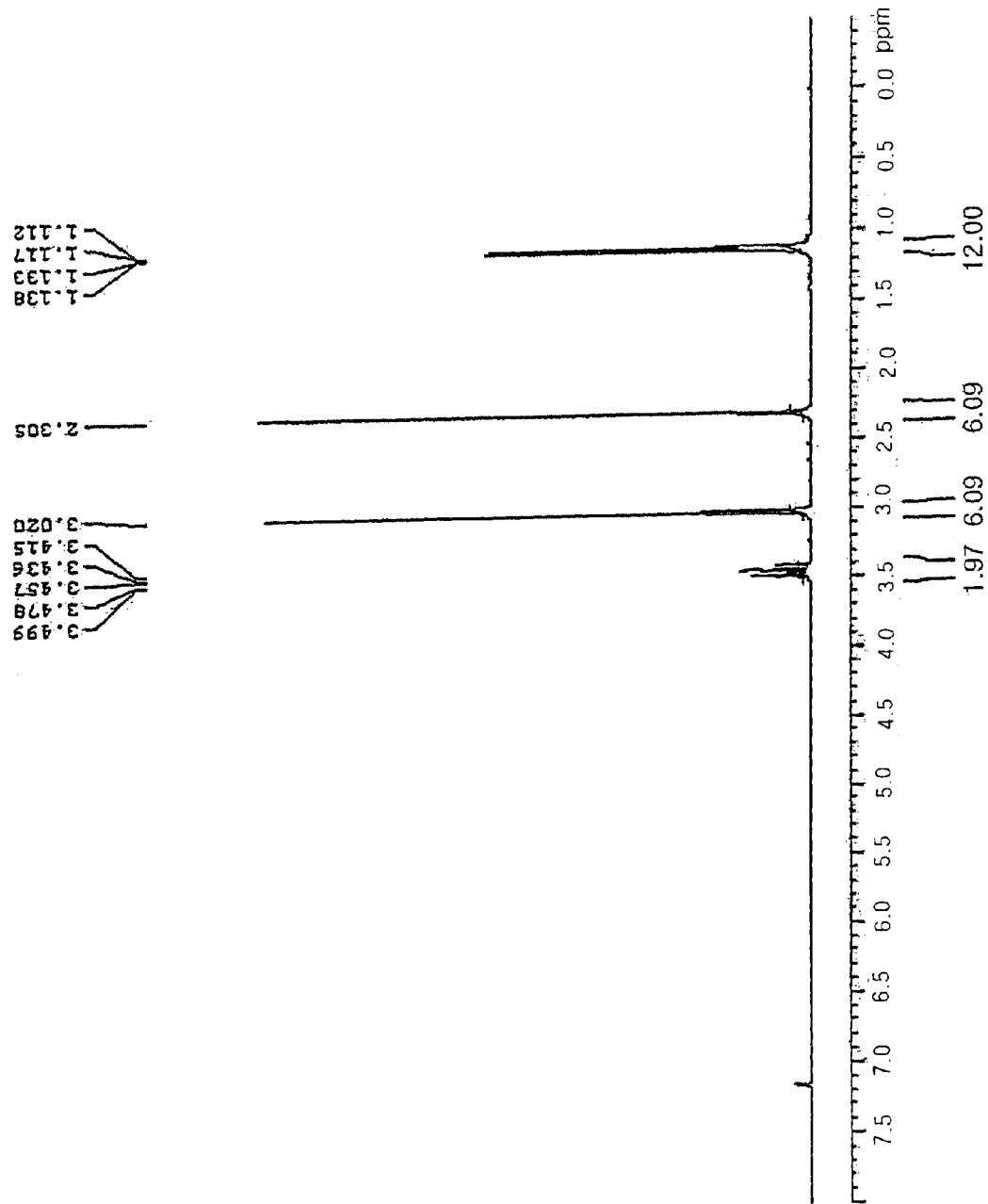
FIG. 4 shows proton nuclear magnetic resonance spectroscopy ($^1H$ NMR) analysis result of the germanium complex prepared in Example 1.
Figure 7:
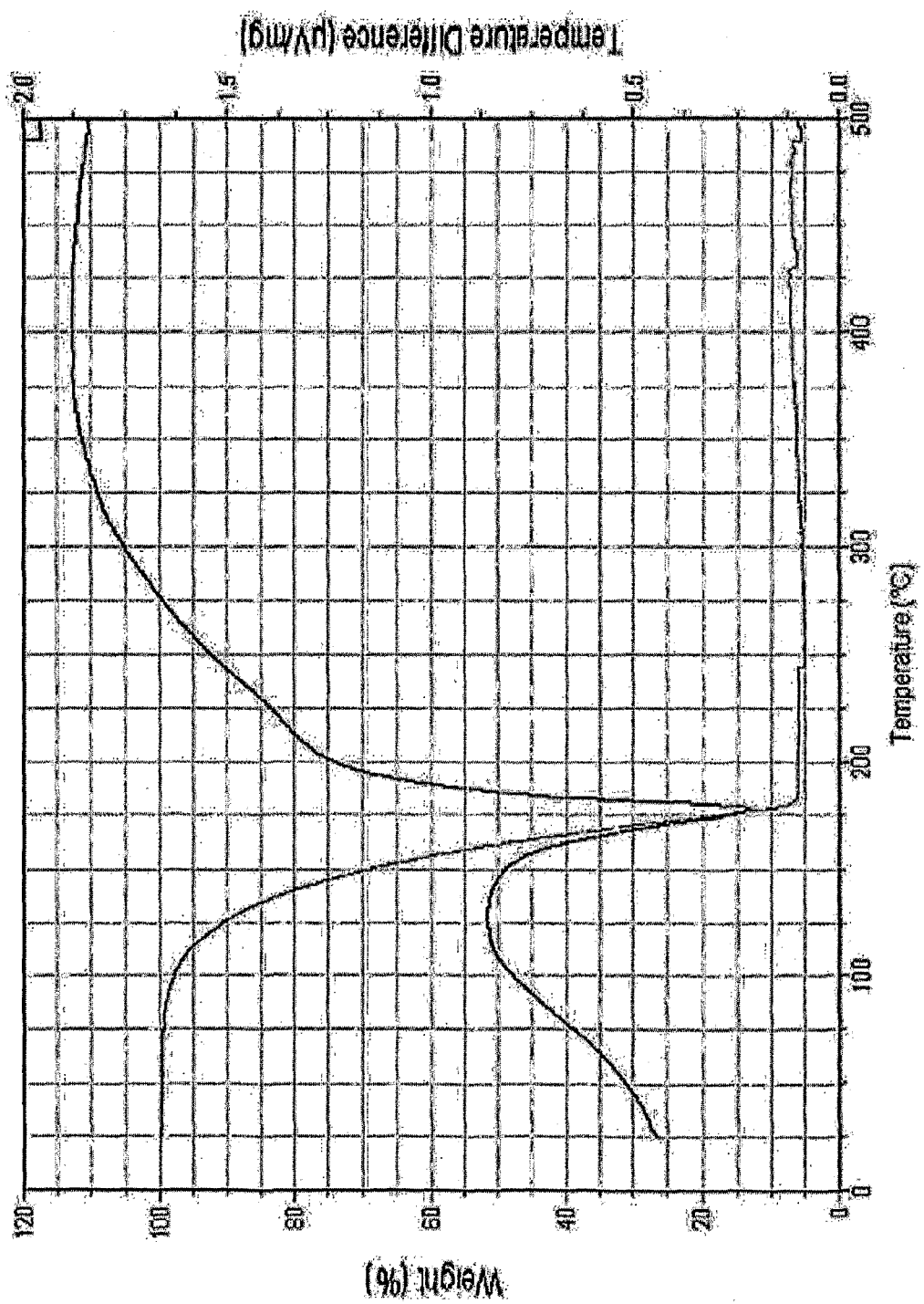
FIG. 7 shows thermogravimetric analysis (TGA) and differential thermal analysis (DTA) results of the germanium complex prepared in Example 1.

The (N,N'-diisopropyl-dimethylguanidyl)(dimethylamino)germanium(II) was subjected to proton nuclear magnetic resonance spectroscopy ($^1H$ NMR). The result is shown in FIG. 4. TGA and differential thermal analysis (DTA) results are shown in FIG. 7.

$^1H$ NMR (ppm, $C_6D_6$,): 1.12 (d, 12H), 2.31 (s, 6H), 3.02 (s, 6H), 3.45 (m, 2H).

Elemental analysis: $C_{11}N_4H_{26}Ge$ [calculated (measured)]: C, 46.04 (45.50); H, 9.13 (9.32); N, 19.52 (20.52).

Example 2

Preparation of (N,N'-diisopropyl-ethylmethylguanidyl)(ethylmethylamino)germanium(II)

Anhydrous n-hexane (50 mL) and ethylmethylamine (5.62 g, 94.98 mmol) were added to a 250 mL Schlenk flask and cooled to −70° C. to prepare solution D. After slowly adding n-butyllithium 2.5 M solution (38.00 mL, 94.98 mmol) dropwise to the solution D, the mixture was slowly warmed to room temperature and stirred for 4 hours to prepare lithium ethylmethylamide solution. The lithium ethylmethylamide solution was cooled to −70° C. and, after slowly adding 1,3-diisopropylcarbodiimide (6.00 g, 47.50 mmol) dropwise, the mixture was slowly warmed to room temperature and stirred for 4 hours to prepare solution E.

In another 250 mL Schlenk flask, anhydrous ether (100 mL) was added to dichlorogermanium-dioxane (7 g, 30.22 mmol) and cooled to −70° C. to prepare solution F. After slowly adding dropwise the reaction solution (solution E) of lithium ethylmethylamide and 1,3-diisopropylcarbodiimide to the solution F, the mixture was slowly warmed to room temperature and stirred for 12 hours. After filtration, solvent was removed from the resulting filtrate at room temperature in vacuum. Thus obtained yellow liquid was distilled in vacuum (78° C./0.1 torr). (N,N'-diisopropyl-ethylmethylguanidyl)(ethylmethylamino)germanium(II) was obtained as colorless liquid.

Thus prepared (N,N'-diisopropyl-ethylmethylguanidyl)(ethylmethylamino)germanium(II) was subjected to TGA. $T_{1/2}$ was 175° C.

$^1$H NMR (ppm, $C_6D_6$,): 0.79 (t, 3H), 1.17 (d, 12H), 1.30 (t, 3H), 2.31 (s, 3H), 2.70 (q, 2H), 3.00 (s, 3H), 3.36 (q, 2H), 3.47 (m, 2H).

Example 3

Preparation of (N,N'-diisopropyl-dimethylguanidyl)(ethylmethylamino)germanium(II)

Anhydrous ether (60 mL) and lithium dimethylamide (1.21 g, 23.7 mmol) were added to a 250 mL Schlenk flask and cooled to −70° C. to prepare solution G. After slowly adding 1,3-diisopropylcarbodiimide (3.27 g, 25.90 mmol) dropwise to the solution G, the mixture was slowly warmed to room temperature and stirred for 4 hours to prepare solution H.

In another 250 mL Schlenk flask, anhydrous ether (100 mL) was added to dichlorogermanium-dioxane (5.00 g, 21.6 mmol) and cooled to −70° C. After slowly adding dropwise the reaction solution (solution H) of lithium dithethylamide and 1,3-diisopropylcarbodiimide, the mixture was slowly warmed to room temperature and stirred for 12 hours to obtain (N,N'-diisopropyl-dimethylaminoguanidyl)(chloro)germanium.

To prepare lithium ethylmethylamide solution, anhydrous n-hexane (50 mL) and ethylmethylamine (LiNEtMe, 1.40 g, 23.70 mmol) were added to another 250 mL Schlenk flask. The mixture was cooled to −70° C. and, after slowly adding n-butyllithium 2.5 M solution (9.48 mL, 23.70 mmol) dropwise, slowly warmed to room temperature and stirred for 4 hours to prepare lithium ethylmethylamide solution (solution I). The previously synthesized (N,N'-diisopropyl-dimethylguanidyl)(chloro)germanium was cooled to −70° C. and slowly added dropwise to thus prepared lithium ethylmethylamide solution (solution I). The mixture was slowly warmed to room temperature and stirred for 12 hours.

After filtration, solvent was removed from the resulting filtrate at room temperature in vacuum. Thus obtained yellow liquid was distilled in vacuum (112° C./0.1 torr). (N,N'-diisopropyl-dimethylguanidyl)(ethylmethylamino)germanium (II) was obtained as yellow liquid.

Figure 5:
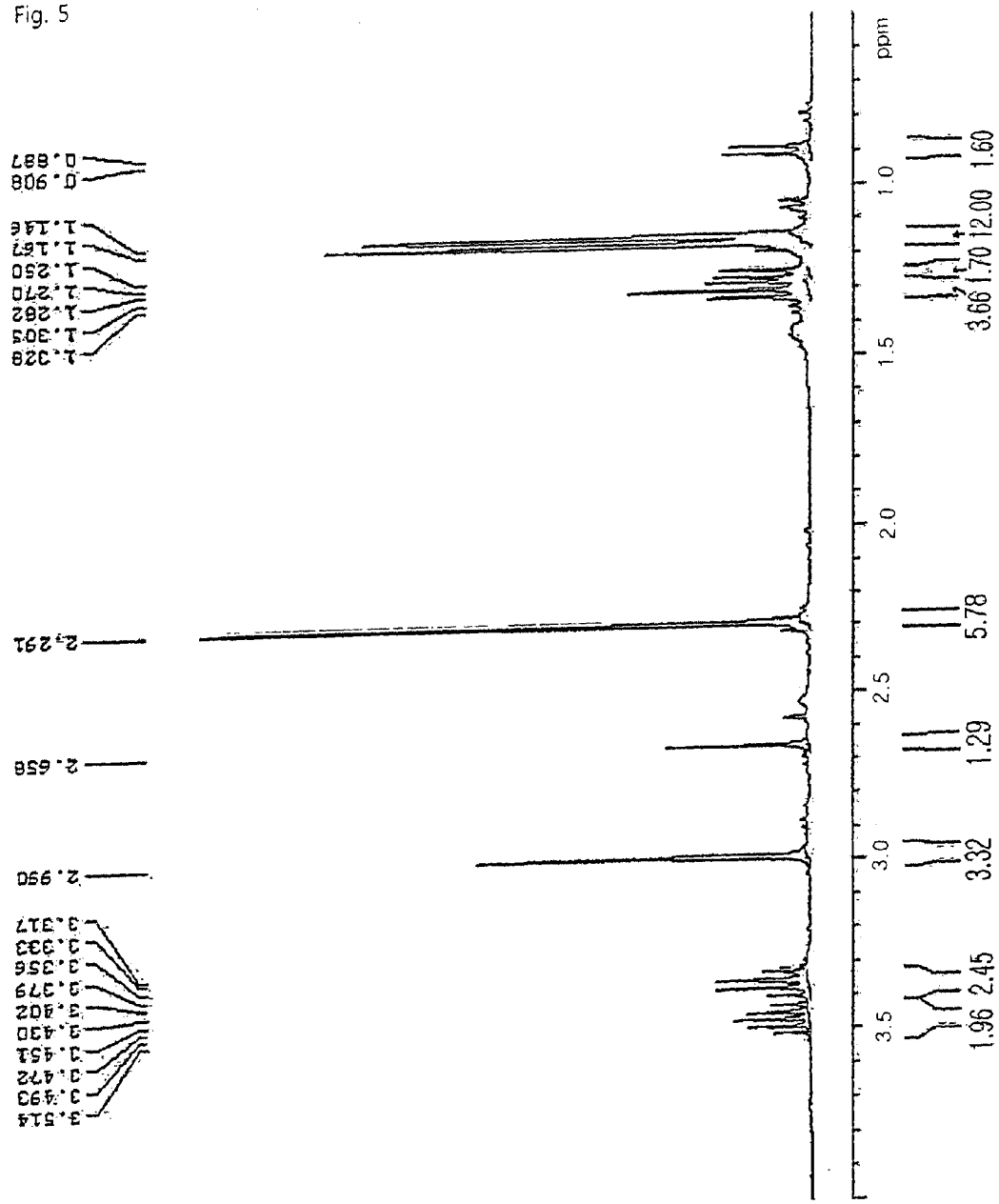
FIG. 5 shows $^1H$ NMR analysis result of the germanium complex prepared in Example 3.
Figure 8:
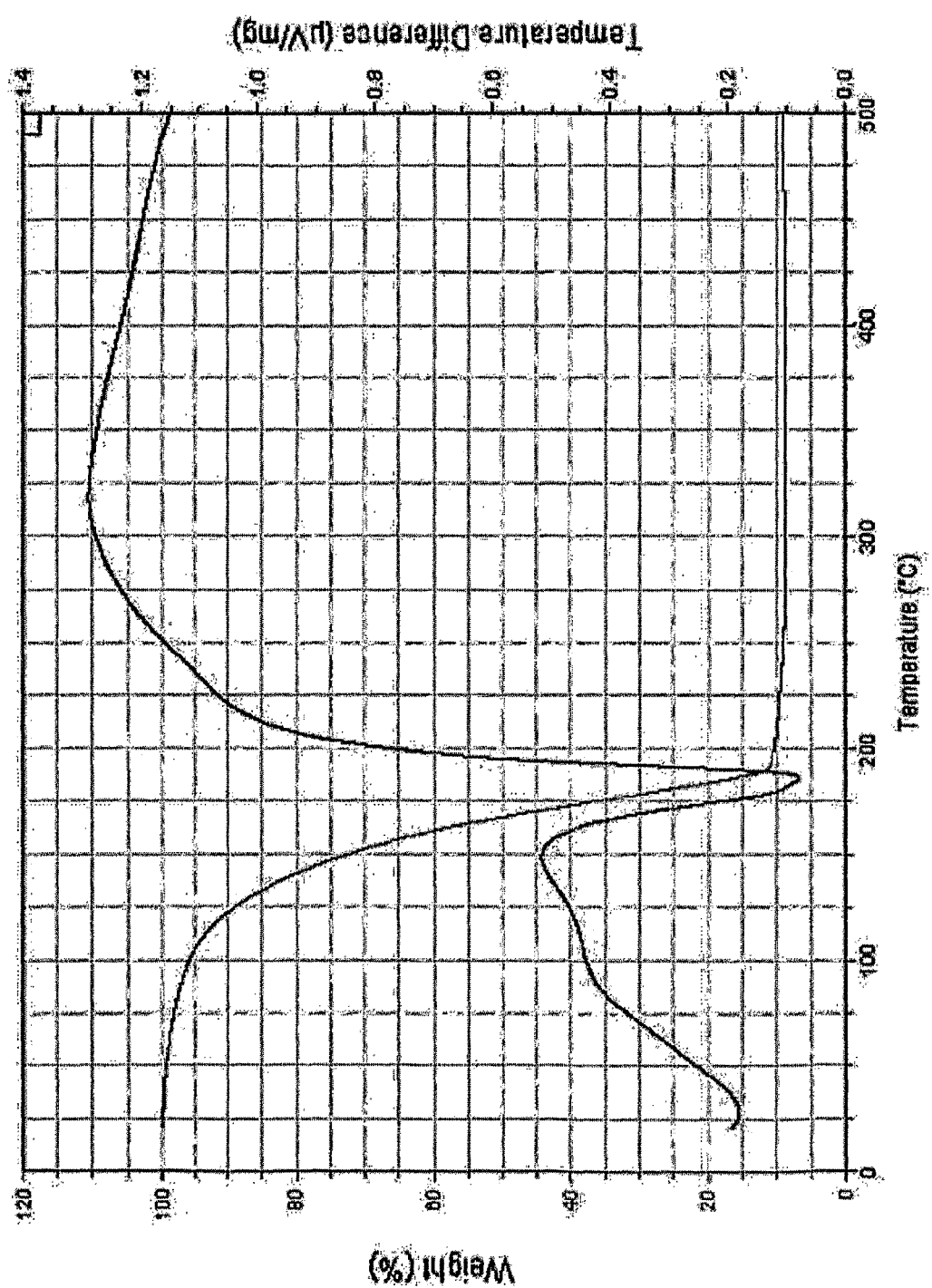
FIG. 8 shows TGA and DTA results of the germanium complex prepared in Example 3.

Thus prepared N,N'-diisopropyl-dimethylguanidyl)ethylmethylamino)germanium(II) was subjected to TGA. $T_{1/2}$ was 166° C. The N,N'-diisopropyl-dimethylguanidyl)(ethylmethylamino)germanium(II) was subjected to $^1$H NMR analysis. The result is shown in FIG. 5. TGA and DTA results are shown in FIG. 8.

$^1$H NMR (ppm, $C_6D_6$,): 1.15 (d, 12H), 1.30 (t, 3H), 2.29 (s, 6H), 2.99 (s, 3H), 3.36 (q, 2H), 3.47 (m, 2H).

Example 4

Preparation of (N,N'-diisopropyl-methylamidyl)(ethylmethylamino)germanium(II)

Anhydrous ether (50 mL) and 1,3-diisopropylcarbodiimide (3.3 g, 25.91 mmol) were mixed in a 250 mL Schlenk flask and, after cooling to −70° C., methyllithium 1.6 M solution (15.00 mL, 23.75 mmol) was slowly added dropwise to prepare solution J. The solution J was slowly warmed to room temperature and stirred for 4 hours to prepare N,N'-diisopropyl-methylamidyllithium salt. In another 250 mL Schlenk flask, dichlorogermanium-dioxane (7 g, 30.22 mmol) and anhydrous ether (100 mL) were mixed and cooled to −70° C. to prepare dichlorogermanium solution.

After slowly adding dropwise the N,N'-diisopropyl-methylamidyllithium salt solution to the dichlorogermanium solution, the mixture was slowly warmed to room temperature and stirred for 4 hours to prepare (N,N'-diisopropyl-methylamidyl)(chloro)germanium.

To prepare lithium ethylmethylamide solution, anhydrous n-hexane (50 mL) and ethylmethylamine (1.40 g, 23.70 mmol) were added to another 250 mL Schlenk flask and cooled to −70° C. To the cooled solution of hexane and ethylmethylamine, n-butyllithium 2.5 M solution (9.48 mL, 23.70 mmol) was slowly added dropwise. The mixture was slowly warmed to room temperature and stirred for 4 hours to prepare lithium ethylmethylamide. The previously synthesized (N,N'-diisopropyl-methylamidyl)(chloro)germanium was cooled to −70° C. and the lithium ethylmethylamide solution prepared above was slowly added dropwise. The mixture was warmed to room temperature and stirred for over 12 hours. After filtration, solvent was removed from the resulting filtrate at room temperature in vacuum. Thus obtained yellow liquid was distilled in vacuum (82° C./0.1 torr). (N,N'-diisopropyl-methylamidyl)(ethylmethylamino)germanium(II) was obtained as colorless liquid.

Figure 6:
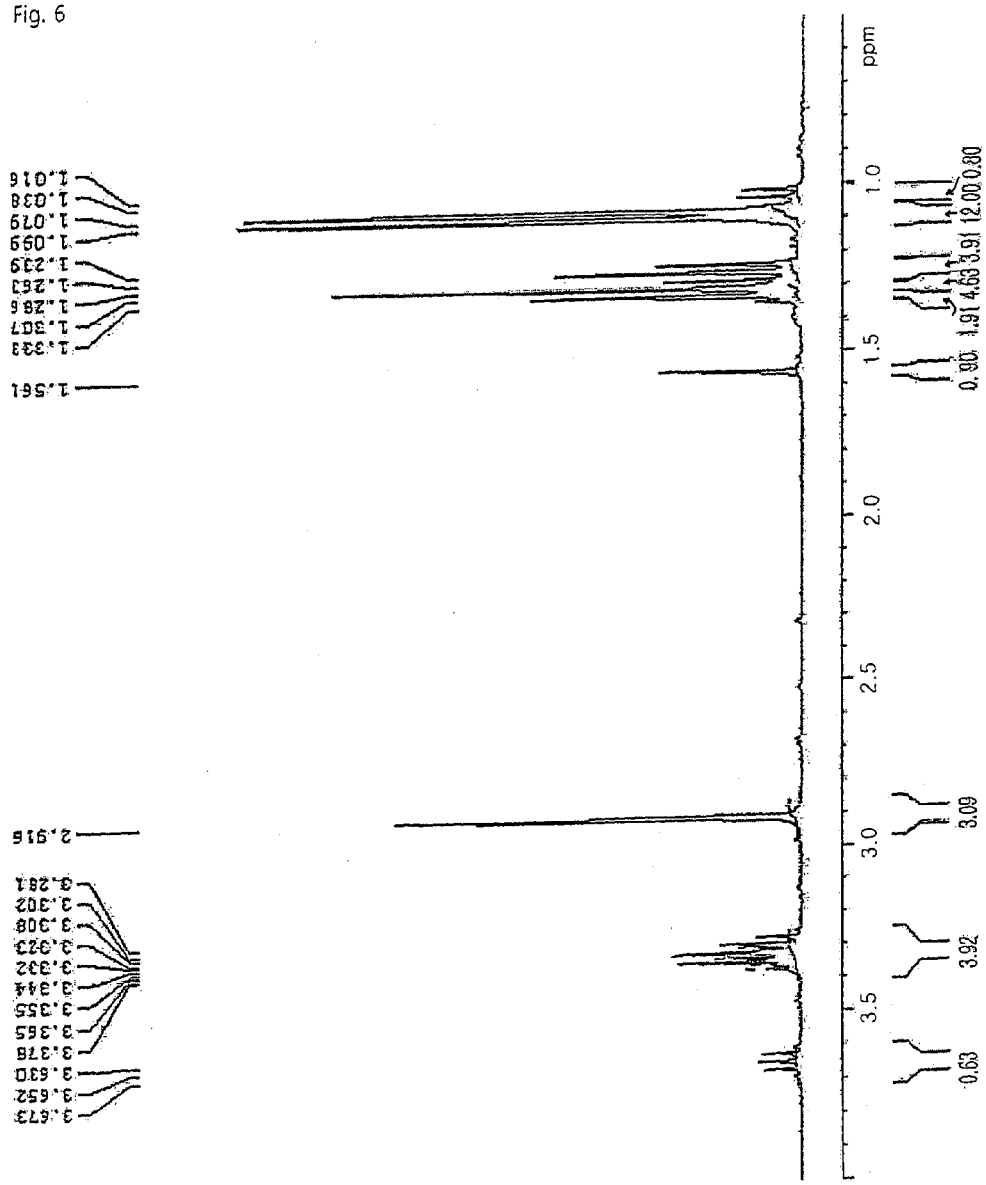
FIG. 6 shows $^1H$ NMR analysis result of the germanium complex prepared in Example 4.

Thus prepared (N,N'-diisopropyl-methylamidyl)(ethylmethylamino)germanium(II) was subjected to TGA. $T_{1/2}$ was 158° C. The (N,N'-diisopropyl-methylamidyl)(ethylmethylamino)germanium(II) was subjected to $^1$H NMR analysis. The result is shown in FIG. 6.

$^1$H NMR (ppm, $C_6D_6$,): 1.08 (d, 12H), 1.26 (t, 3H), 1.29 (s, $^3$H), 3.34 (q, 2H), 3.34 (m, 2H).

Example 5

Preparation of (N,N'-diisopropyl-methylamidyl)(dimethylamino)germanium(II)

Anhydrous ether (100 mL) and 1,3-diisopropylcarbodiimide (5.99 g, 47.50 mmol) were added to a 250 mL Schlenk flask and cooled to −70° C. To the resulting 1,3-diisopropylcarbodiimide solution, 1.6 M methyllithium solution (29.68 mL, 47.50 mmol) was slowly added dropwise. After warming to room temperature, the mixture was stirred for 4 hours to prepare N,N'-diisopropylmethylamidyllithium salt.

In another 250 ml Schlenk flask, dichlorogermanium-dioxane (10 g, 43.20 mmol) and anhydrous ether (100 mL) were added and cooled to −70° C. After slowly adding dropwise the N,N'-diisopropylmethylamidyllithium salt, the mixture was warmed to room temperature and stirred for 4 hours to prepare (N,N'-diisopropyl-methylamidyl)(chloro)germanium.

In another 250 mL Schlenk flask, anhydrous ether (100 mL) and lithium dimethylamide (2.42 g, 46.50 mmol) were cooled to −70° C. and the (N,N'-diisopropyl-methylamidyl) (chloro)germanium prepared above was slowly added dropwise. The resulting N,N'-diisopropyl-methylamidyl)(chloro) germanium solution was warmed to room temperature and stirred for 12 hours. After filtration, solvent was removed from the resulting filtrate at room temperature in vacuum. Thus obtained yellow liquid was distilled in vacuum (78° C./0.1 torr). (N,N'-diisopropyl-methylamidyl)(dimethylamino)germanium(II) was obtained as yellow liquid.

Figure 9:
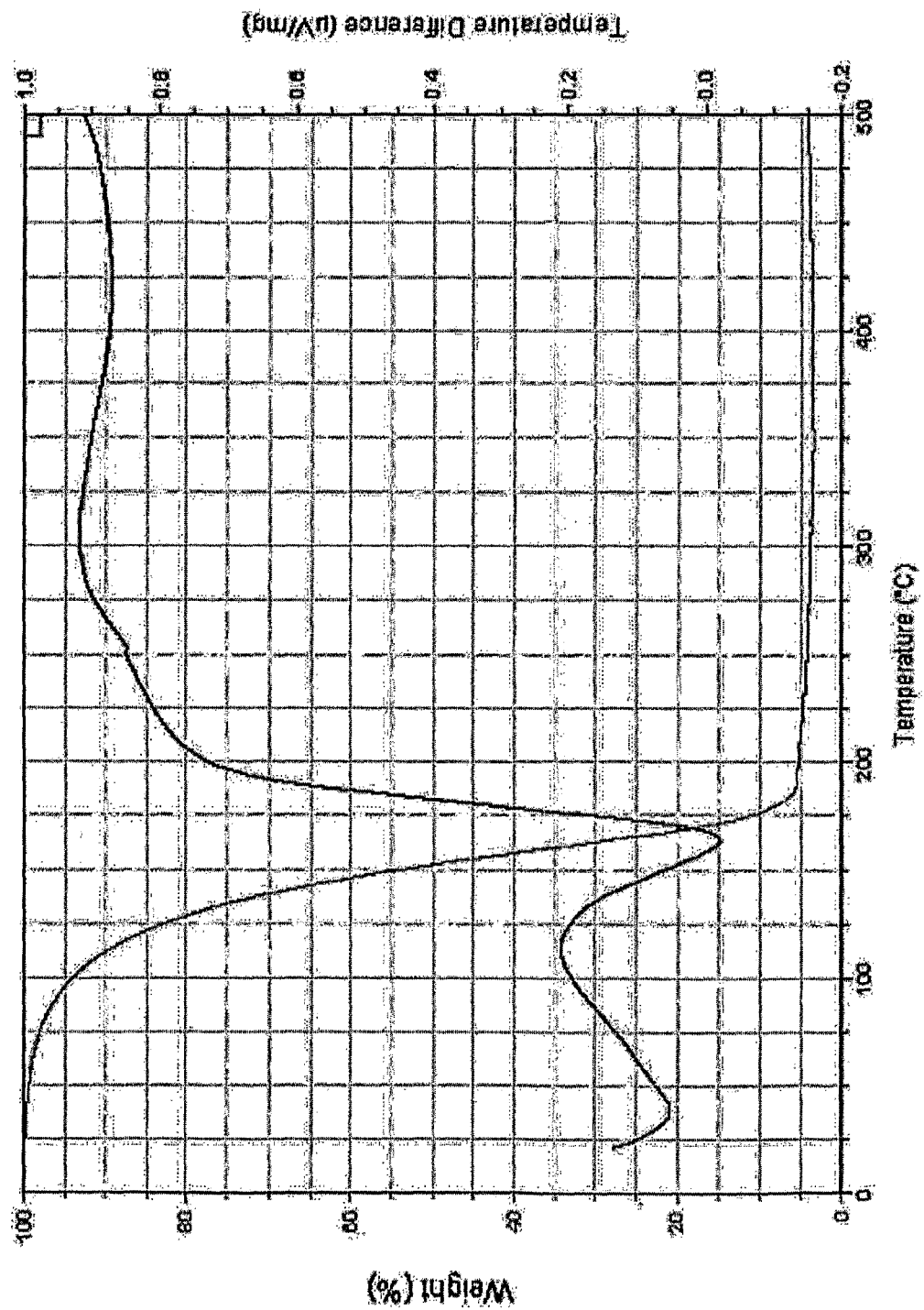
FIG. 9 shows TGA and DTA results of the germanium complex prepared in Example 5.

Thus prepared (N,N'-diisopropyl-methylamidyl)(dimethylamino)germanium(II) was subjected to TGA. $T_{1/2}$ was 154° C. TGA and DTA results of the germanium complex are shown in FIG. 9.

$^1$H NMR (ppm, $C_6D_6$,): 1.07 (d, 12H), 1.30 (s, 3H), 3.00 (s, 6H), 3.30 (m, 2H).

Example 6

Preparation of (N,N'-diisopropyl-dimethylguanidyl) (t-butyl)germanium(II)

Anhydrous ether (50 mL) and lithium dimethylamide (2.43 g, 47.49 mmol) were mixed in a 250 mL Schlenk flask and cooled to −70° C. After slowly adding dropwise 1,3-diisopropylcarbodiimide (6.54 g, 51.81 mmol) to the mixture solution of anhydrous ether and lithium dimethylamide, the mixture was slowly warmed to room temperature and stirred for 4 hours. In another 250 mL Schlenk flask, dichlorogermanium-dioxane (10.00 g, 43.17 mmol) and anhydrous ether (100 ml) were mixed and cooled to −70° C. To the resulting dichlorogermanium-dioxane solution, the reaction solution of lithium dimethylamide and 1,3-diisopropylcarbodiimide prepared above was slowly added dropwise. The mixture was slowly warmed to room temperature and stirred for 12 hours to prepare (N,N'-diisopropyl-dimethylguanidyl)(chloro)germanium.

Thus synthesized (N,N'-diisopropyl-dimethylguanidyl) (chloro)germanium was cooled to −70° C. and, after slowly adding dropwise t-butyllithium solution (9.50 mL, 47.49 mmol), the resulting mixture was slowly warmed to room temperature and allowed to react for over 12 hours. After filtration, solvent was removed from the resulting filtrate at room temperature in vacuum. Thus obtained yellow liquid was distilled in vacuum (120° C./0.1 torr). (N,N'-diisopropyl-dimethylguanidyl)(t-butyl)germanium(II) was obtained as colorless liquid.

Thus prepared (N,N'-diisopropyl-methylguanidyl) t-butyl) germanium(II) was subjected to TGA. $T_{1/2}$ was 170° C.

$^1$H NMR (ppm, $C_6D_6$,): 1.11 (q, 12H), 1.31 (s, 9H), 2.29 (s, 6H), 3.51 (m, 2H).

Example 7

Deposition of Germanium Thin Film

A germanium thin film was formed by metal organic chemical vapor deposition (MOCVD) using the (N,N'-diisopropyl-dimethylguanidyl)(dimethylamino)germanium(II) synthesized in Example 1 as source material and using argon as carrier gas. The (N,N'-diisopropyl-dimethylguanidyl) (dimethylamino)germanium(II) was carried to a $TiN/SiO_2/Si$ substrate inside a chamber at about 50 sccm using argon as the carrier gas. The source temperature was maintained at about 60° C., and the substrate temperature at 300° C. Deposition was carried out for 1 hour. Deposition pressure was maintained at 3 torr.

Figure 2:
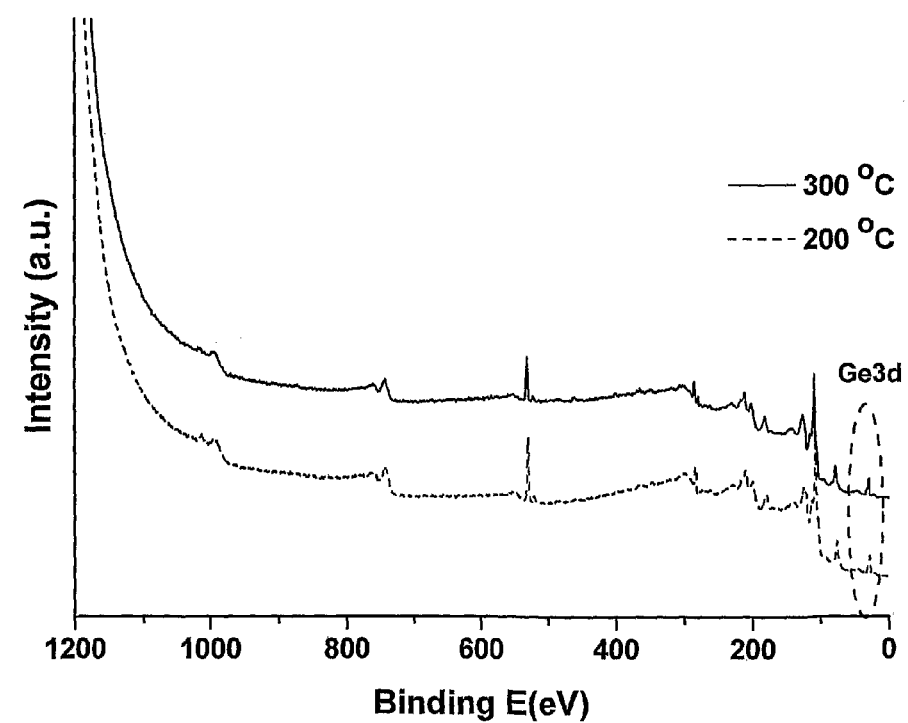
FIG. 2 shows X-ray photoelectron spectroscopy (XPS) analysis result of the germanium thin films deposited in Example 7 and Example 9 according to the present invention.
Figure 3:
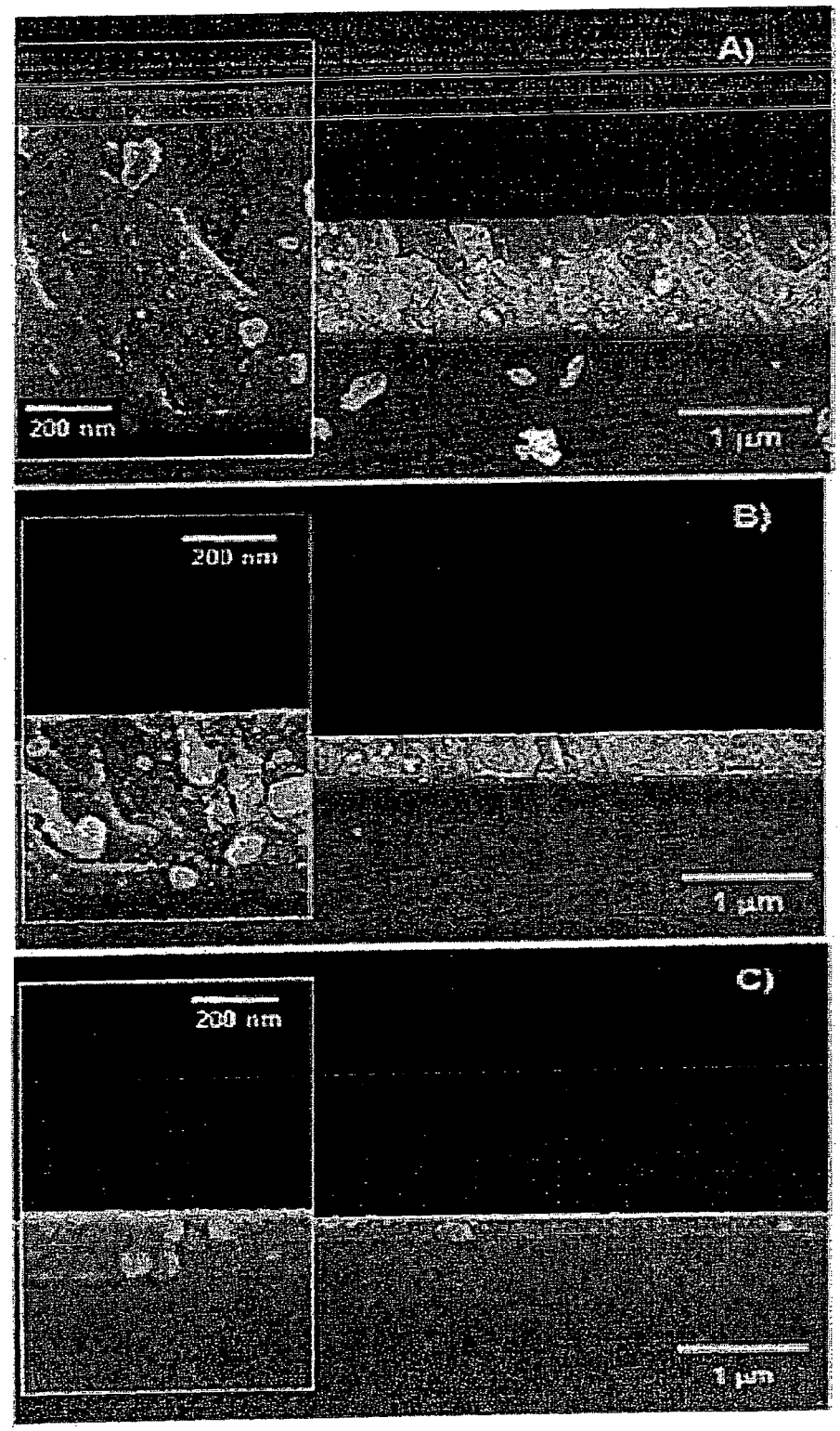
FIG. 3A) shows scanning electron microscopy (SEM) analysis result of the germanium thin film deposited in Example 7, FIG. 3 B) shows SEM analysis result of the germanium thin film deposited in Example 8, and FIG. 3 C) shows SEM analysis result of the germanium thin film deposited in Example 9.

X-ray diffraction (XRD) analysis result of thus deposited germanium thin film is shown in FIG. 1, X-ray photoelectron spectroscopy (XPS) analysis result shown in FIG. 2, and scanning electron microscopy (SEM) analysis result in FIG. 3 A). The thin film had a thickness of about 1 μm.

Example 8

Deposition of Germanium Thin Film

Deposition was carried out in a similar manner as Example 7, except that the substrate temperature was maintained at 250° C.

SEM analysis result of thus deposited germanium thin film is shown in FIG. 3 B).

Example 9

Deposition of Germanium Thin Film

Deposition was carried out in a similar manner as Example 7, except that the substrate temperature was maintained at 200° C.

XRD analysis result of thus deposited germanium thin film is shown in FIG. 1, XPS analysis result shown in FIG. 2, and SEM analysis result in FIG. 3 C). As seen from FIG. 3, the germanium thin film prepared according to the present invention was an amorphous germanium thin film. The XPS analysis result of FIG. 2 shows that thin film deposition could be accomplished in Example 9. Accordingly, it was confirmed that the germanium complex according to the present invention could be deposited to form a thin film even at a relatively low temperature of 200° C.

The invention claimed is:

1. A germanium complex represented by Chemical Formula 1:

[Chemical Formula 1]

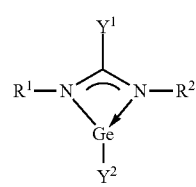

wherein $Y^1$ and $Y^2$ are independently selected from $R^3$, $NR^4R^5$ or $OR^6$, and $R^1$ through $R^6$ independently represent $(C_1$-$C_7)$alkyl.

2. The germanium complex according to claim 1, wherein $Y^1$ and $Y^2$ independently represent —$N(CH_3)_2$, —$N(CH_3)$ $(CH_2CH_3)$, —$CH_3$ or —$C(CH_3)_3$.

3. The germanium complex according to claim 2, which is selected from the following structures:

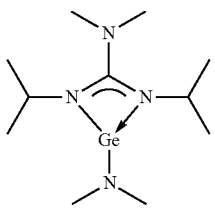 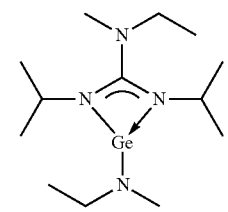

-continued

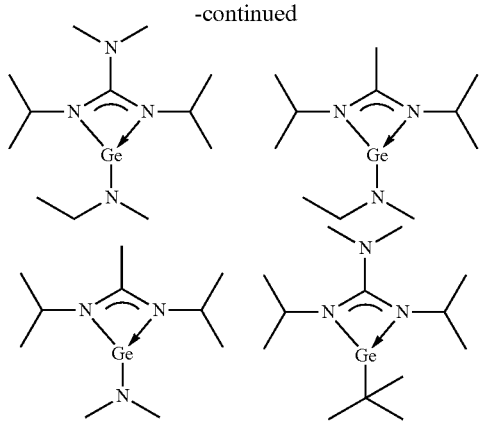

4. A method for preparing a germanium thin film, comprising:
   injecting the germanium complex according to claim 3 to a substrate provided in a reactor to prepare a germanium thin film by chemical vapor deposition or atomic layer deposition.

5. A method for preparing a germanium thin film, comprising:
   injecting the germanium complex according to claim 2 to a substrate provided in a reactor to prepare a germanium thin film by chemical vapor deposition or atomic layer deposition.

6. The germanium complex according to claim 1, wherein $R^1$ through $R^2$ independently represent methyl, ethyl, propyl or t-butyl.

7. A method for preparing a germanium thin film, comprising:
   injecting the germanium complex according to claim 6 to a substrate provided in a reactor to prepare a germanium thin film by chemical vapor deposition or atomic layer deposition.

8. A method for preparing a germanium thin film, comprising:
   injecting the germanium complex according to claim 1 to a substrate provided in a reactor to prepare a germanium thin film by chemical vapor deposition or atomic layer deposition.

9. The method for preparing a germanium thin film according to claim 8, wherein the temperature of the substrate is from 150 to 350° C.

10. A method for preparing a germanium complex, comprising:
    reacting an alkali metal salt represented by Chemical Formula 3 with an alkylcarbodiimide ($R^1NCNR^2$) compound represented by Chemical Formula 4 to prepare a complex represented by Chemical Formula 5; and
    adding to the complex represented by Chemical Formula 5 a germanium(II) halide and an alkali metal salt represented by Chemical Formula 6 to prepare a germanium complex represented by Chemical Formula 1:

$$M^1Y^1 \quad \text{[Chemical Formula 3]}$$

$$R^1NCNR^2 \quad \text{[Chemical Formula 4]}$$

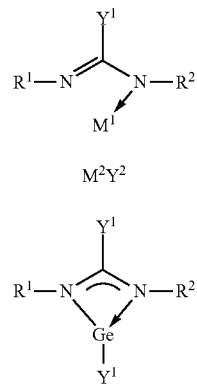

[Chemical Formula 5]

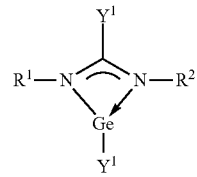

[Chemical Formula 6]

[Chemical Formula 7]

wherein $M^1$ and $M^2$ independently represent an alkali metal, $Y^1$ and $Y^2$ are independently selected from $R^3$, $NR^4R^5$ or $OR^6$, and $R^1$ through $R^6$ independently represent $(C_1-C_7)$alkyl.

11. The method for preparing a germanium complex according to claim 10, wherein $Y^1$ and $Y^2$ independently represent —$N(CH_3)_2$, —$N(CH_3)(CH_2CH_3)$, —$CH_3$ or —$C(CH_3)_3$, and $M^1$ and $M^2$ independently represent lithium, sodium or potassium.

12. The method for preparing a germanium complex according to claim 10, or wherein the alkylcarbodiimide is 1,3-diisopropylcarbodiimide.

13. The method for preparing a germanium complex according to claim 10, wherein the germanium complex represented by Chemical Formula 1 or Chemical Formula 7 is selected from the following structures:

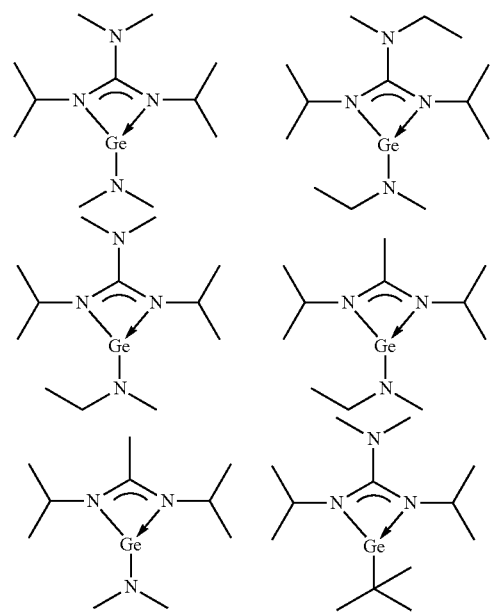

14. The method for preparing a germanium complex according to claim 10, wherein the germanium(II) halide is $Ge(II)Br_2$, $Ge(II)Cl_2$(dioxane) or $Ge(II)I_2$.

15. A method for preparing a germanium complex, comprising:

reacting an alkali metal salt represented by Chemical Formula 3 with an alkylcarbodiimide ($R^1NCNR^2$) compound represented by Chemical Formula 4 to prepare a complex represented by Chemical Formula 5; and adding to the complex represented by Chemical Formula 5 a germanium(II) halide to prepare a germanium complex represented by Chemical Formula 7:

[Chemical Formula 3]

$M^1Y^1$

[Chemical Formula 4]

$R^1NCNR^2$

[Chemical Formula 5]

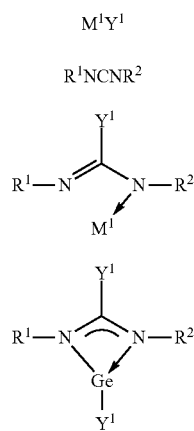

[Chemical Formula 7]

wherein $M^1$ represents an alkali metal, $Y^1$ is selected from $R^3$, $NR^4R^5$ or $OR^6$, and $R^1$ through $R^6$ independently represent ($C_1$-$C_7$)alkyl.

16. The method for preparing a germanium complex according to claim 15, wherein $Y^1$ represents —$N(CH_3)_2$, —$N(CH_3)(CH_2CH_3)$, —$CH_3$ or —$C(CH_3)_3$, and $M^1$ represents lithium, sodium or potassium.

17. The method for preparing a germanium complex according to claim 15, wherein the alkylcarbodiimide is 1,3-diisopropylcarbodiimide.

18. The method for preparing a germanium complex according to claim 15, wherein the germanium complex represented by Chemical Formula 1 or Chemical Formula 7 is selected from the following structures:

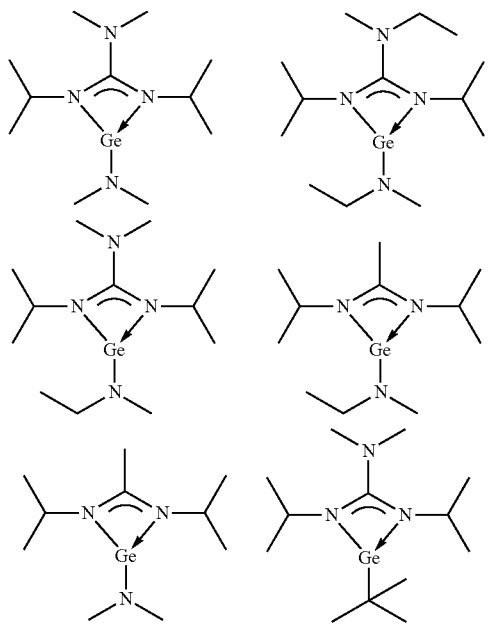

.

19. The method for preparing a germanium complex according to claim 15, wherein the germanium(II) halide is Ge(II)Br$_2$, Ge(II)Cl$_2$(dioxane) or Ge(II)I$_2$.

* * * * *

UNITED STATES PATENT AND TRADEMARK OFFICE
CERTIFICATE OF CORRECTION

PATENT NO.        : 8,663,736 B2                                        Page 1 of 1
APPLICATION NO.   : 13/143621
DATED             : March 4, 2014
INVENTOR(S)       : Jae Sun Jung et al.

It is certified that error appears in the above-identified patent and that said Letters Patent is hereby corrected as shown below:

In the Claims

Column 14, Lines 10-16, Claim 10, delete "  " and insert -- --

Column 14, Line 29, Claim 12, delete "claim 10, or" and insert -- claim 10, --

Signed and Sealed this
Twenty-second Day of July, 2014

Michelle K. Lee
*Deputy Director of the United States Patent and Trademark Office*